United States Patent [19]
Landis

[11] Patent Number: 5,692,522
[45] Date of Patent: Dec. 2, 1997

[54] FACE SHIELD APPARATUS

[75] Inventor: Timothy J. Landis, Loomis, Calif.

[73] Assignee: OP-D-OP, Inc., Roseville, Calif.

[21] Appl. No.: 659,282

[22] Filed: Jun. 6, 1996

[51] Int. Cl.⁶ ................................................ A61F 11/00
[52] U.S. Cl. ................................ 128/857; 128/858; 2/15
[58] Field of Search ............................ 128/846, 857, 128/858; 2/9, 10, 15, 428, 429, 431, 424, 426, 427, 6.2, 6.3, 6.5

[56] References Cited

U.S. PATENT DOCUMENTS

| | | |
|---|---|---|
| 3,120,002 | 2/1964 | Blumenthal ................................ 2/9 |
| 3,383,707 | 5/1968 | McNeill . | |
| 3,629,870 | 12/1971 | Paisley ................................... 2/15 |
| 4,843,643 | 7/1989 | Parissenti ............................... 128/857 |
| 5,469,229 | 11/1995 | Greenbaum ............................ 2/15 |
| 5,503,497 | 4/1996 | Landis et al. . | |

*Primary Examiner*—Michael A. Brown
*Attorney, Agent, or Firm*—John P. O'Banion

[57] ABSTRACT

A face shield apparatus having a head worn frame assembly, and a detachable and replaceable face shield coupled thereto. The frame assembly comprises a pair of generally parallel, spaced apart side members which are joined to a front member, which is supported by the wearer's nose or forehead. Articulating tails are included on the frame side members. One or more posts are provided on the frame assembly which pivotally engage one or more sockets associated with the face shield and provide for pivotal adjustment of the face shield relative to the frame assembly.

21 Claims, 7 Drawing Sheets

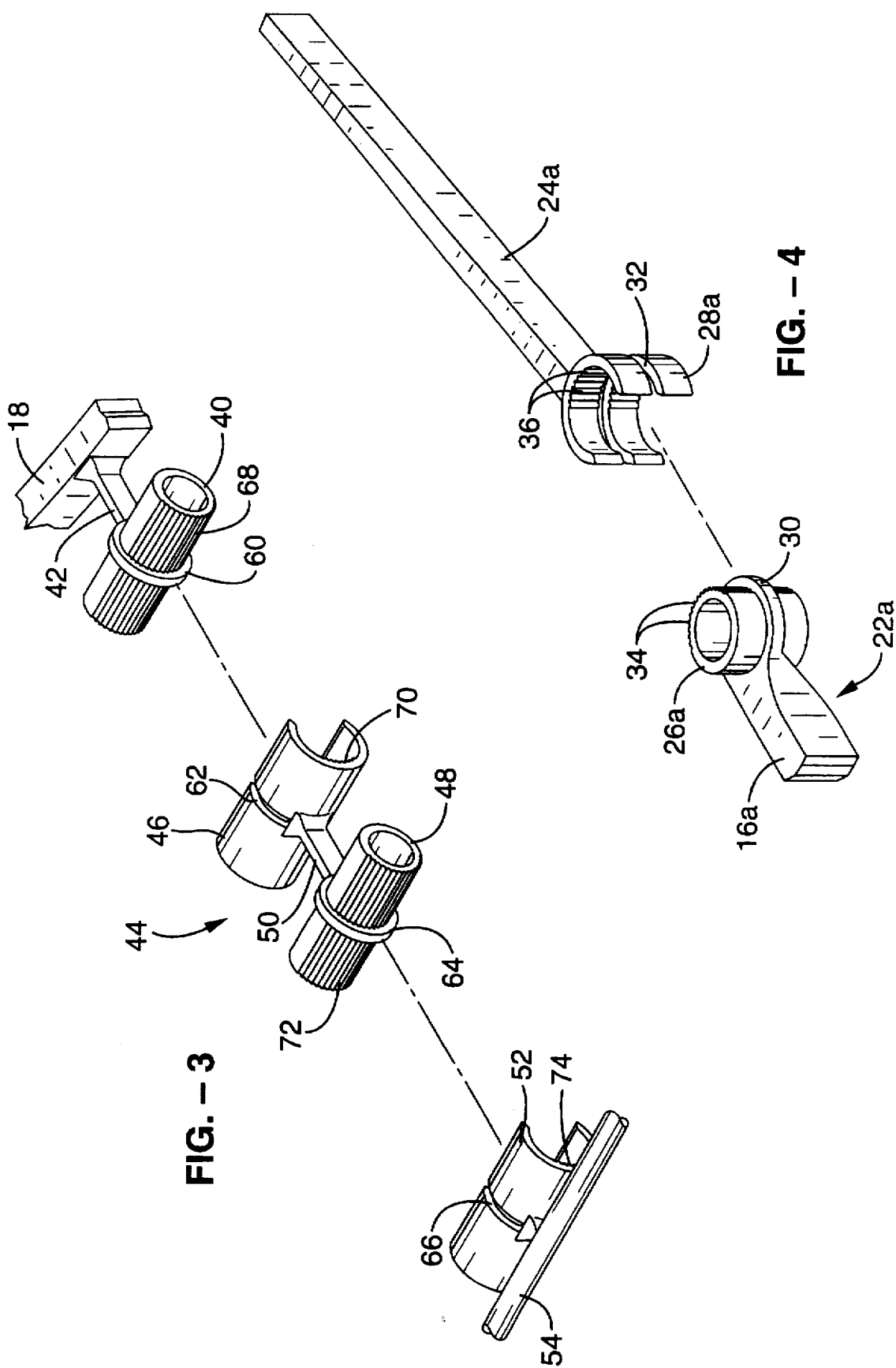

FACE SHIELD APPARATUS

BACKGROUND OF THE INVENTION

1. Field of the Invention

This invention pertains generally to face shields and face and eye protection devices, and more particularly to a face shield apparatus having a head-worn, light-weight support frame with a face shield pivotally and detachable coupled thereto.

2. Description of the Background Art

Face shield devices are used in numerous professions to protect the eyes and face of wearers from various occupational hazards. Use of face shields has grown substantially in dental and medical professions, in response to the spread of AIDS and like infectious diseases, to prevent infection from body fluid splatter.

Face shields are typically supported on a wearer's head by a head band or head visor apparatus, with the face shield generally attached to the head band or visor such that the face shield is positioned in front of the wearer's face. In one frequently-used type of face shield device the face shield is suspended directly from the edge or brim of a head worn visor to provide protection to a wearer's face. Other types of face shield devices provide for pivotal attachment of the face shield to the sides of a head band or visor.

A frequent problem experienced by users of face shields is that currently known face shield devices are uncomfortable to wear, particularly for extended periods of time. Wearers must frequently reposition the head band or visor which supports the face shield in order to minimize discomfort. Face shield devices which rely on head bands or head visors for support tend to cause perspiration under the band or strap, causing additional discomfort. Further, physicians, dentists, welders, and other persons who rely on face shields frequently have both hands occupied in difficult or complex procedures, and cannot free their hands to positionally adjust the face shield apparatus to reduce discomfort.

Another deficiency common to conventional face shield devices is that the face shields are not readily detachable from the devices. Face shields used in the medical and dental professions must be exchanged between treatment of each patient to avoid cross-infection or cross-contamination of patients. Many currently used face shield devices do not provide for easy removal or interchange of face shields, so that contaminated face shields can be sterilized or disposed.

Still another problem present in many conventional face shield devices is that the face shields cannot undergo pivotal adjustment while on the wearer's head, or pivotal adjustment is difficult to make while the face shield is being worn.

Accordingly, there is a need for a face shield apparatus which is comfortable to wear, which is light weight, which provides for quick and easy detachment and re-attachment of face shields, and which provides for quick and easy pivotal adjustment of face shields while on the wearer's head. The present invention satisfies these needs, as well as others, and generally overcomes the deficiencies found in prior devices.

SUMMARY OF THE INVENTION

The present invention pertains to a face shield apparatus which is lightweight and comfortable to wear, which provides for quick and easy detachment and replacement of face shields, and which provides for pivotal positional adjustment of a face shield while on the wearer's head. In its most general terms, the invention comprises a head worn frame assembly, a face shield, and means for pivotally coupling the face shield to the frame assembly.

By way of example and not of limitation, the frame assembly generally comprises a pair of spaced apart, substantially parallel elongated side members, and a front member coupled to the side members. A nose bridge or support is preferably included on the front member, and the side members preferably are hinged to the front member in a manner similar to conventional eye-glass frames. Articulating tails are included on the ends of the side members to aid in holding the frame assembly on a wearer's head. The face shield is detachable from the frame assembly and interchangeable. Preferably, the face shield comprises a thin piece of transparent, resilient and inexpensive polymer sheet material such as polyethylene terephthalate or polystyrene. The face shield is structured and configured to conform to the wearer's face.

The pivotal coupling means preferably comprises a generally cylindrical tongue or post attached to the frame assembly by a support arm. The pivotal coupling means also preferably comprises a link member having a socket which pivotally engages the post on the frame assembly, and post coupled to the socket by a connecting arm. A socket associated with the face shield pivotally engages the post of the link member. The socket associated with the face shield is preferably attached to a mounting rod having a plurality of studs or protrusions. A plurality of matching holes or slots are included on the face shield to reversibly snap fit the studs on the mounting rod. Teeth or serrations may be included on the outer surfaces of the posts and inner surfaces of the sockets to allow for pivotal articulation of the face shield relative to the frame assembly in precise incremental units. Alternatively, a cylindrical post may be coupled to the mounting rod, and a socket mounted on the frame assembly. One or more link members comprising a connected post and socket may be included with the coupling means.

The invention is used by attaching a face shield to the mounting rod by snap fitting the studs of the mounting rod into the corresponding holes in the face shield, engaging the socket on the mounting rod and post of the link member, and engaging the socket of the link member with the post on the frame assembly so that the face shield is coupled to the frame assembly. The frame assembly is then positioned on a wearer's head with the side members generally adjacent the sides of the wearer's head, with the front member adjacent to the wearer's forehead, and with the nose support positioned on the wearer's nose. The articulating tails on the side members of the frame assembly are positioned to support the frame assembly on the wearer's head. The face shield may be positioned relative to the frame assembly and the wearer's head by pushing on the face shield, thereby exerting force on the engaged sockets and posts so that the sockets and posts pivotally reposition relative to each other, thereby allowing the socket and tongue and thus the attached face shield to be pivotally adjusted.

An object of the invention is to provide a face shield apparatus which is lightweight and comfortable to wear.

Another object of the invention is to provide a face shield apparatus wherein the face shield is readily detachable and interchangeable.

Another object of the invention is to provide a face shield apparatus which provides quick, easy and accurate pivotal adjustment of the face shield while worn on the wearer's head.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 3 is a perspective view in detail of the pivotal coupling arrangement connecting the face shield and frame assembly of FIG. 1.

FIG. 4 is a perspective view in detail of the pivotal coupling arrangement connecting a side member and articulating tail of the frame assembly of FIG. 1.

DESCRIPTION OF THE PREFERRED EMBODIMENTS

Figure 1:
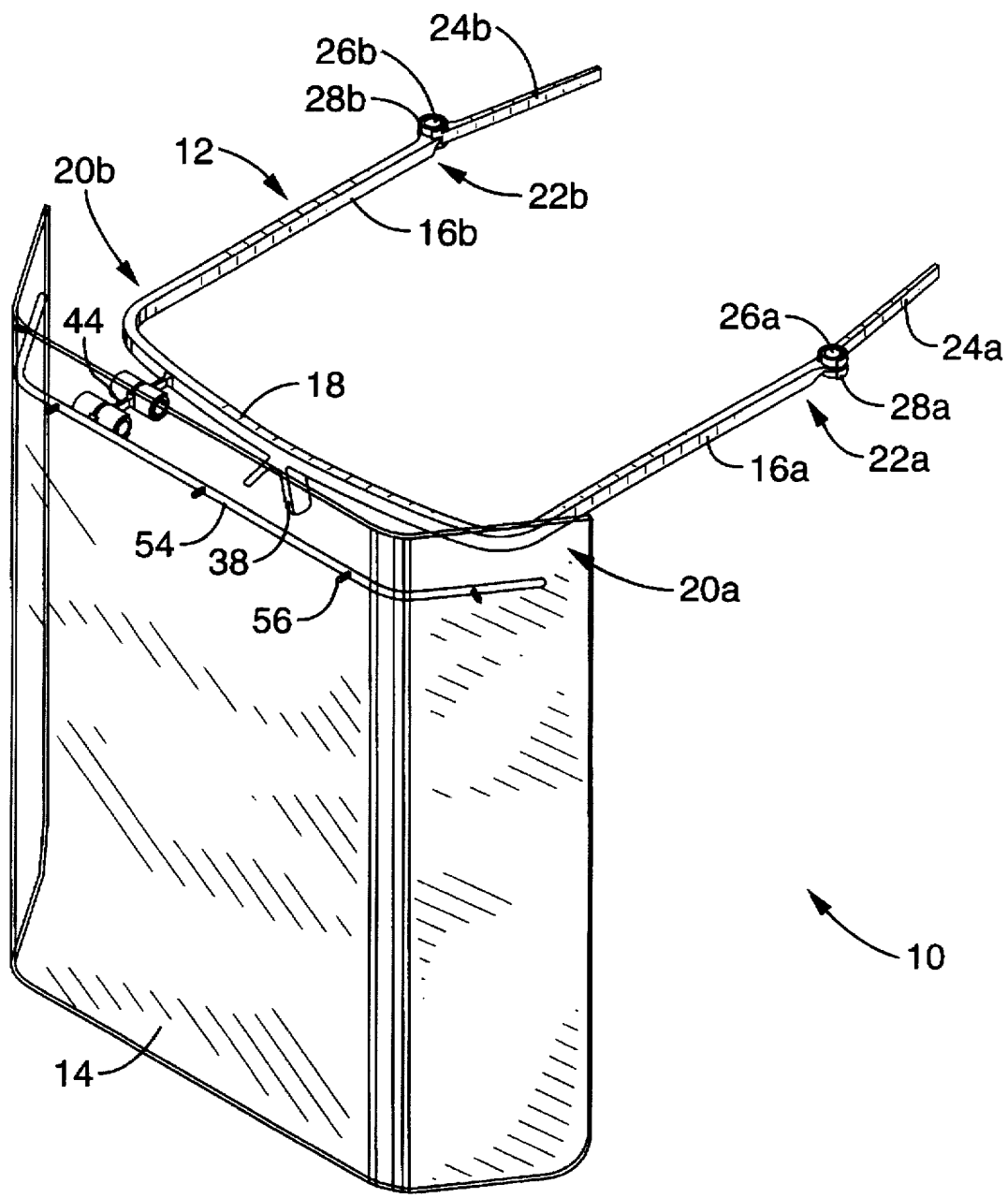
FIG. 1 is a perspective view of a first embodiment of a face shield apparatus in accordance with the present invention.
Figure 2:
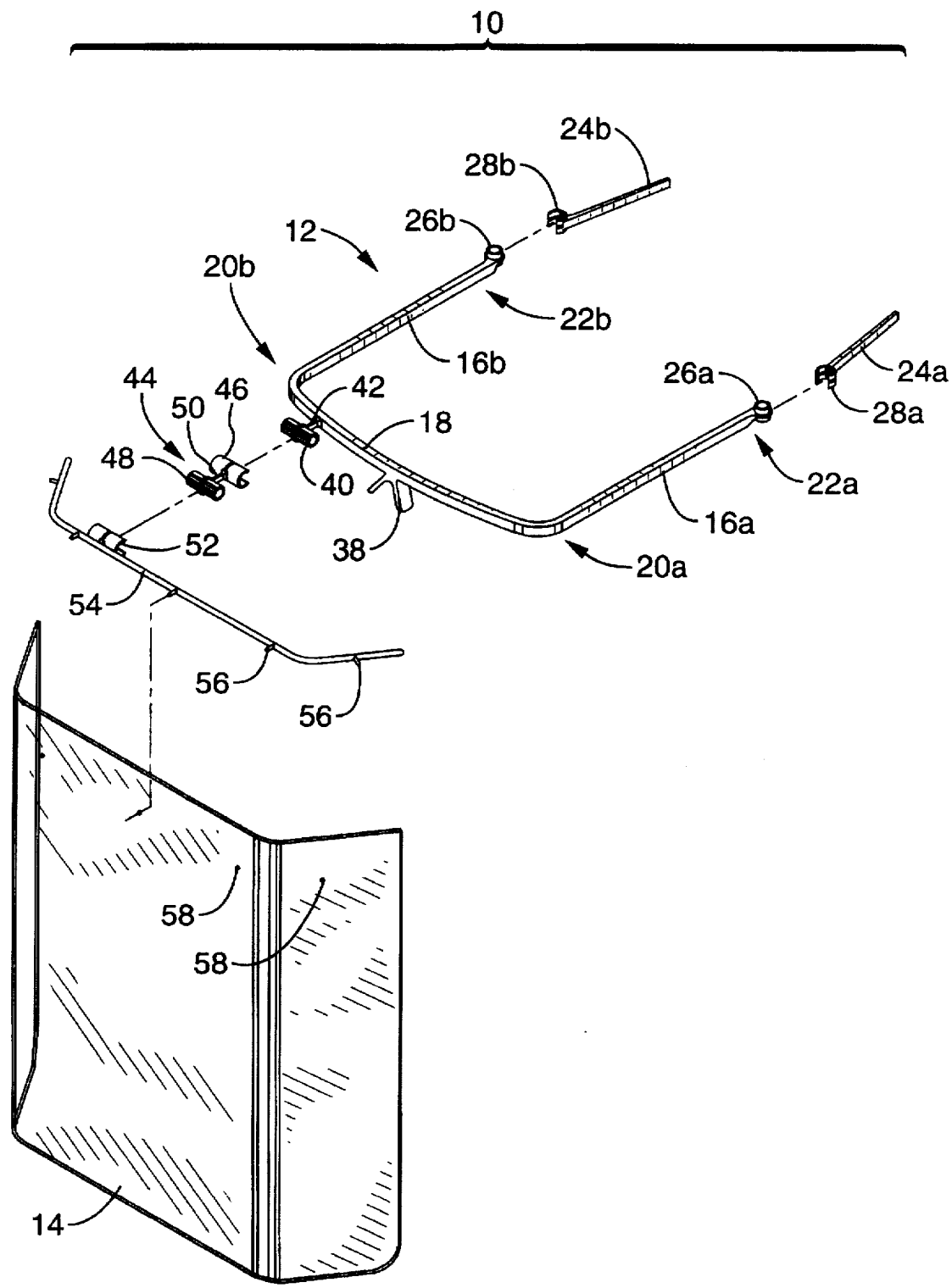
FIG. 2 is an exploded view of the face shield apparatus of FIG. 1.

Referring more specifically to the drawings, for illustrative purposes the present invention is embodied in the apparatus generally shown in FIG. 1 through FIG. 8, where like reference numerals denote like parts. It will be appreciated that the apparatus may vary as to configuration and as to details of the parts without departing from the basic concepts as disclosed herein.

Referring now to FIG. 1 through FIG. 4, a first embodiment 10 of a face shield apparatus in accordance with the present invention is generally shown. The apparatus 10 includes a frame assembly 12 which is worn on a person's head, and a face shield 14 which detachably couples to frame assembly 12. Face shield 14 is structured and configured to provide protection to a wearer's face, and may vary in shape according to different applications of the invention. Face shield 14 is preferably of lightweight construction, and is made of thin, transparent, resilient, inexpensive polymeric sheet material such as polystyrene, acrylic, polyethylene terephthalate, polycarbonate, or like polymeric material.

Frame assembly 12 preferably comprises first and second side members 16a, 16b and a front member 18. Side members 16a, 16b and front member 18 are preferably elongated in shape as shown, and are of resilient construction. Preferably, side members 16a, 16b and front member 18 are made of durable, heat resistant and chemical resistant polymeric material which may be sterilized by autoclaving. Internal wires or metal strip (not shown) may be included within front member 18 and side members 16a, 16b to provide reinforcement. Side member 16a includes a first end 20a and a second end 22a, and side member 16b likewise includes a first end 20b and a second end 22b. Side member 16a is coupled at first end 20a to front member 18, and side member 16b is similarly coupled to front member 18 at first end 20b as shown. Side members 16a, 16b may be pivotally coupled to front member 18 by hinge mechanisms (not shown) as in conventional eye glass frames, or alternatively, side members 16a, 16b may be joined to front member 18 in a fixed position. Side members 16a, 16b preferably are parallel to each other and are spaced apart sufficiently to accommodate a wearer's head therebetween.

Side members 16a, 16b and front member 18 are shown as joined together in a manner which imparts a generally rectangular shape to frame assembly 12 similar to that of conventional eye glass frames. However, different structures and configurations for frame assembly 12 may be used with the invention. For example, side members 16a, 16b and/or front member 18 may be curved in shape in order to define a generally oval or circular-shaped frame assembly 12. Curved regions (not shown) on side members 16a, 16b may be provided to accommodate the ears of a wearer while frame assembly 12 is worn on the wearer's head.

Preferably, first and second articulating tails 24a, 24b are included on ends 22a, 22b of first and second side member 16a, 16b respectively of frame assembly 12, to aid in holding frame assembly 12 on the wearer's head. Referring more particularly to FIG. 4, means for pivotally coupling articulating tails 24a, 24b to side members 16a, 16b are provided with the invention, and preferably comprise generally cylindrically shaped posts 26a, 26b mounted on ends 22a, 22b of first and second side members 16a, 16b. The coupling means additionally comprises sockets 28a, 28b on articulating tails 24a, 24b, with sockets 28a, 28b structured and configured to pivotally engage posts 26a, 26b. Sockets 28a, 28b are preferably made of resilient material, and reversibly receive and engage posts 26a, 26b respectively by snap fitting. Laterally extending ridges 30a, 30b are provided on posts 26a, 26b, and laterally extending slots 32a, 32b are included in sockets 28a, 28b respectively. When posts 26a, 26b are engaged in sockets 28a, 28b, lateral ridges 30a, 30b fit within slots 32a, 32b and prevent longitudinal sliding of posts 26a, 26b relative to sockets 28a, 28b which could cause unwanted disengagement of posts 26a, 26b from sockets 28a, 28b. Alternative pivotal coupling means, such as ball and socket joints, pintle and gudgeon arrangements, and like hinge arrangements may also be used to attach articulating hinges 24a, 24b to side members 16a, 16b. Preferably, a plurality of teeth or serrations 34 are included on the outer surface of posts 26a, 26b, and corresponding teeth or serrations 36 included on the inner surface of sockets 28a, 28b. Serration 34 on posts 26a, 26b reversibly engage and intermesh with serrations 36 on sockets 28a, 28b to provide articulating motion of tails 24a, 24b in a ratcheting manner with incremental units of pivotal adjustment. Serrations 34, 36 may be omitted to provide generally smooth articulating motion of articulating tails 24a, 24b, if desired. A flexible or resilient strap (not shown) may be used alternatively or in addition to articulating tails 24a, 24b to aid in holding frame assembly 12 on the wearer's head.

A nose support 38 is included in frame assembly 12 as means for supporting frame assembly 12 on a wearer's face, and is preferably located in the center of front member 18 as shown. Nose support 38 is coupled to front member 18 in a downward facing manner, and is structured and configured to rest on the bridge of a wearer's nose in a manner similar to that of conventional eye glass frames.

Means for coupling face shield 14 to frame assembly 12 are provided with the invention. Referring more particularly to FIG. 3 as well as FIG. 1 and FIG. 2, the coupling means preferably provides for detachable and pivotal coupling of face shield 14 to frame assembly 12, although face shield 14 may alternatively be fixedly coupled to frame assembly 12 if desired. The coupling means preferably comprises a generally cylindrical tongue or post 40 associated with frame assembly 12. Post 40 is coupled to front member 18 of frame assembly 12, preferably by a support arm 42. Post 40 and support arm 42 are shown as positioned generally off-center relative to front member 18 so as not to interfere with nose support 38. However, post 42 may alternatively be centrally mounted onto front member or may be attached to a side member as discussed below in another embodiment of the invention. Post 40 and support arm 42 are preferably integral with front member 18, and made of the same durable, autoclavable polymeric material. Post 40 and/or support arm 42 may alternatively comprise a separate piece or pieces which is mounted onto front member 18 or elsewhere on frame assembly 12 by adhesives or the like.

The coupling means also preferably comprises a link member 44. Link member 44 includes a socket 46 and generally cylindrical post 48 coupled to socket 46 by a connecting arm 50. Socket 46 is structured and configured to reversibly and pivotally engage or receive post 40. Socket 46 is preferably made of a resilient material which allows socket 46 to reversibly snap fit onto post 40. Link member 44 is preferably an integral piece of heat sterilizable, durable polymeric material. The coupling means also comprises a socket 52 associated with face shield 14, with socket 52 structured and configured to reversibly and pivotally engage or receive post 48 on link member 44. Socket 52 is also preferably made of a resilient material to allow reversible snap fit onto post 40. Snap fitting means for detachably coupling socket 52 to face shield 14 are preferably included with the invention. The snap fitting means preferably includes a mounting rod or bar 54, to which socket 52 is coupled. Referring again to FIG. 1 and FIG. 2, mounting rod 54 detachably couples to face shield 14 by means of a plurality of studs 56 which reversibly snap fit into a plurality of corresponding openings or holes 58 in face shield 14. Mounting rod 54 and socket 52 are preferably integral portions of a single piece of durable, light weight, autoclavable, polymeric material. Socket 52 may be positioned centrally relative to mounting bar 54, rather than off-centered as shown. An internal wire or metal strip reinforcement (not shown) may be included on mounting rod 54. Socket 52 may alternatively be integral with face shield 14, or attached thereto by adhesives or numerous snap fitting arrangements. Various additional attachment means for associating socket 52 with face shield 14 will be apparent to persons skilled in the art. As mentioned above, the preferred face shield 14 of the invention is made of thin, resilient polymeric material, and thus it is preferable to associate socket 52 with face shield 14 in a manner wherein the weight of face shield 14 is supported at numerous points over a relatively large area, as is accomplished by the elongated mounting rod 54 and plurality of studs 56 thereon.

While post 40 is engaged in socket 46, socket 46 and post 40 can pivotally move or articulate relative to each other in response to application of force as described below. Post 48 and socket 52 likewise undergo pivotal motion relative to each other upon application of force. Referring again to FIG. 3, a lateral ridge 60 encircles post 40, and fits within a corresponding lateral groove or slot 62 in socket 46 when socket 46 and post 40 are engaged, to prevent socket 46 from sliding off of post 40. A lateral ridge 64 is provided on post 48, which fits within a corresponding lateral groove or slot 66 in socket 52, to prevent socket 52 from sliding off of post 48 while socket 52 and post 48 are engaged.

Preferably, a plurality of teeth, serrations or ridges 68 are included on the outer surface of post 40, which engage and intermesh with a corresponding plurality of serrations 70 on the inner surface of socket 46. Serrations 68, 70 provide for ratcheting articulation of socket 46 relative to post 40 in incremental units when post 40 pivots within socket 46. A plurality of serrations 72 are likewise included on the outer surface of post 48 and a plurality of serrations 74 are included on the inner surface of socket 52 to allow ratcheting articulation. Serrations 68, 70, 72, 74 may alternatively be omitted from posts 40, 48 and sockets 46, 52 to allow smooth rather than ratcheting pivotal movement.

Interfitting post and socket pivotal coupling arrangements as related above are described in more detail in U.S. Pat. No. 5,503,497 issued on Apr. 2, 1996 owned by the assignee hereof, which is incorporated by reference herein.

It should be readily apparent to persons skilled in the art that link member 44 may be omitted from the coupling means of the invention, and socket 52 may pivotally engage post 40 directly. However, the use of link member 44 provides additional degrees of pivotal adjustment and serves to hold face shield 14 further from the wearer's face, thereby preventing face shield 14 from bumping against the wearer's nose. It is contemplated that a second or additional posts may be included on frame assembly 12, either on front member 18 or side members 16a, 16b, and a second or additional sockets may be included on mounting bar 54 or otherwise associated with face shield 14. Additionally, the location of post 40 and socket 52 could be interchanged, with socket 52 positioned on frame assembly 12 and post 40 joined to mounting bar 54. It is further contemplated that a plurality of link members 44 could be employed with the coupling means of the invention in order to provide additional points of pivotal adjustment and to hold the face 14 further from frame assembly 12 and the wearer's face generally.

Numerous other coupling means are also contemplated for use in pivotally attaching face shield 14 to frame assembly 12. For example, the use of one or more bendable support arms may be used to connect face shield 14 to frame assembly 12, with pivotal motion of face shield 14 relative to frame assembly 12 obtained by physically bending the support arms into a desired position or shape. A ball and socket hinge arrangement may be used as an alternative to the post and socket hinge arrangement related above, to provide additional degrees of pivotal motion. Various other conventional hinge arrangements, such as pintle and gudgeon assemblies, are also suitable for coupling face shield 14 onto frame assembly 12. Face shield 14 may also be detachably or fixedly coupled to frame assembly 12 in a non-articulating fashion, although the use of coupling means which provide for pivotal motion of face shield 14 relative to frame 12 is preferred.

The face shield apparatus 10 is used by snap fitting the studs 56 on mounting rod 54 into the corresponding slots or holes 58 on face shield 14, thereby attaching socket 52 to face shield 14. Post 48 on link member 44 is engaged within socket 52, and post 40 on frame member is engaged within socket 46 on link member 44. The user of the invention then places frame assembly 12 onto his or her head such that side members 16a, 16b are generally adjacent the sides of the head, front member 18 is generally adjacent to the user's forehead, and nose support 38 rests on the bridge of the user's nose. Articulating tails 24a, 24b are pivotally positioned into a desired position to hold frame assembly 12 on the user's head. Side members 16a, 16b may be positioned apart at a distance such that side members 16a, 16b tensionally engage the user's head in order to assist in holding frame assembly 12 into place.

The position of face shield 14 may be pivotally adjusted relative to frame assembly 12 while the apparatus 10 is on the user's head by pushing on or otherwise applying force to face shield 14, which causes socket 52 to pivot about post 48, and/or socket 46 to pivot about post 40, depending upon the location and manner in which force is applied to face shield 14. As socket 52 pivots about post 48, serrations 74 within socket 52 disengage from serrations 72 on post 48 and reposition relative to each other. When face shield 14 has pivoted to a desired position, the force is removed from face shield 14, and serrations 72, 74 again intermesh, retaining the adjusted position of face shield 14. Likewise, as socket 46 pivots about post 48, serrations 68, 70 reposition relative to each other, and when the force is removed from face shield 14, serrations 68, 70 intermesh to retain the adjusted position. Since the preferred face shield 14 is made of thin, light weight, flexible material, face shield will be able to withstand only a small amount of force without bending or otherwise deforming. In order to avoid bending of face shield 14 rather than positional adjustment upon application of force, it is preferably that serrations 68, 70, 72, 74 are relatively small so that only a small application of force is required to disengage intermeshed serrations. Thus, when the user of the invention applies force by pushing on face sheild 14, the desired articulating adjustment of face shield 14 is obtained rather than unwanted bending of face shield 14. Support arm 42 may be varied in length and shape in order to control the distance of face shield 14 from the wearer's face. Connecting arm 50 on link member 44 can also be varied in length and shape as required for particular applications of the invention. Alternatively, link member 44 may be omitted as described above, although the additional degrees of pivotal motion provided by link member 44 are preferred.

If face shield 14 becomes contaminated or dirty, it can be quickly and easily detached or removed from frame assembly 12 and replaced by disengaging studs 56 from holes 58 in face shield. Alternatively, face shield 14 may be uncoupled from frame assembly 12 by disengaging post 48 from socket 52, and/or disengaging post 40 from socket 46. The contaminated face shield may be disposed of or cleaned or sterilized by autoclaving or other conventional treatment. As mentioned above, mounting bar 54, link member 44, and frame assembly 12 are preferably heat sterilizable, but may alternatively be disposable. A replacement face shield may then be attached to mounting bar 54, and then attached to frame assembly 12. The detachment and replacement of face shield 14 may be carried out without removal of frame assembly 12 from the user's head.

The detachable socket 52 and mounting bar 54, which snap fit onto face shield 14 via studs 56 and holes 58, allow the material and fabrication costs of face shield 14 to be minimized in order to make face shield 14 disposable. Conventional face shield devices generally include means for attaching a face shield to a wearer's head which are integral to the face shield, thus increasing the cost of manufacturing the face shield and making disposal of the face shield unattractive. The present invention, which provides for detachment of socket 52 and mounting bar 54 however, allows use of a face shield 14 which is made solely from inexpensive, disposable polymeric sheet material.

Figure 5:
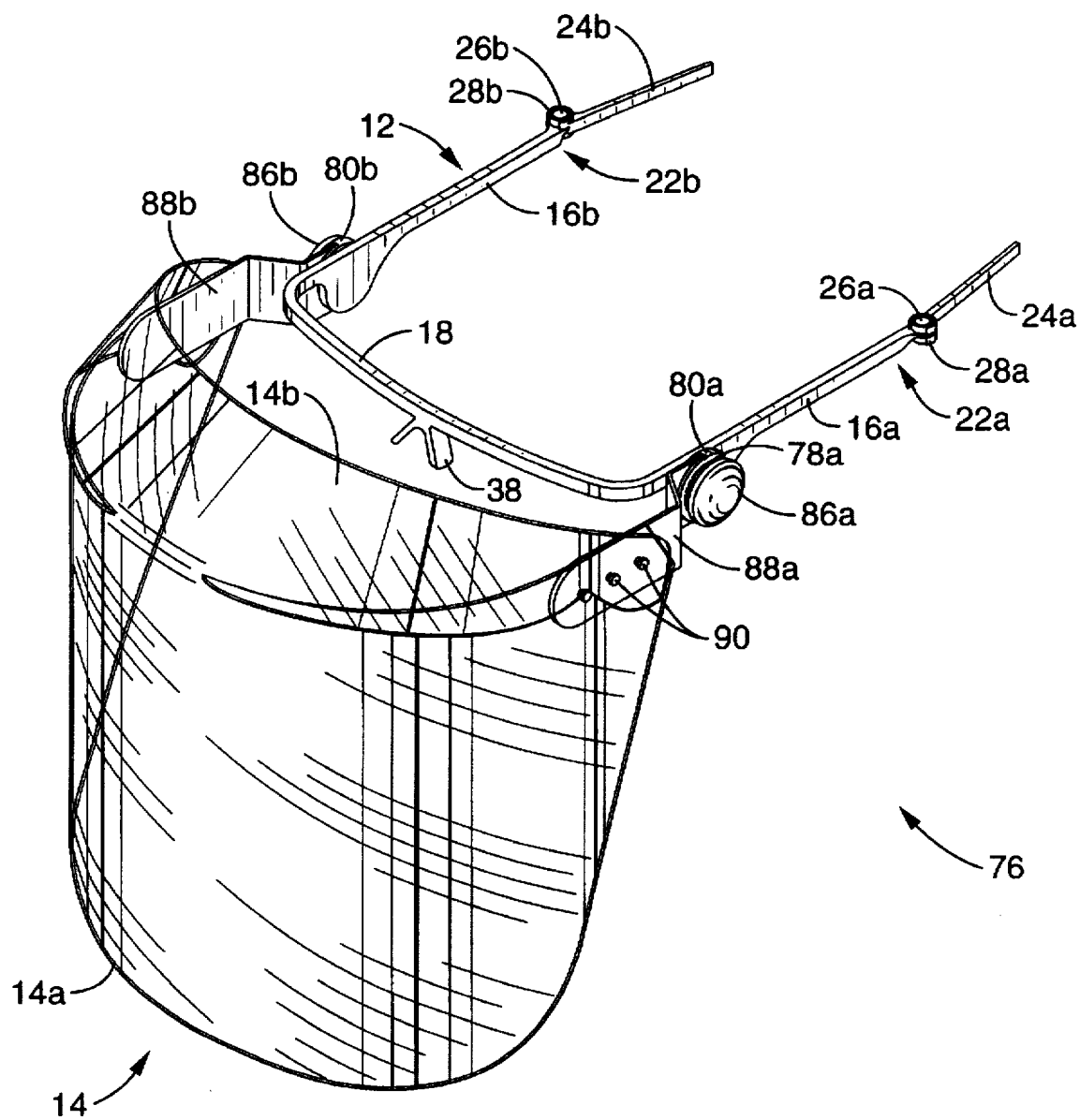
FIG. 5 is a perspective view of an alternative embodiment of a face shield apparatus in accordance with the present invention.
Figure 6:
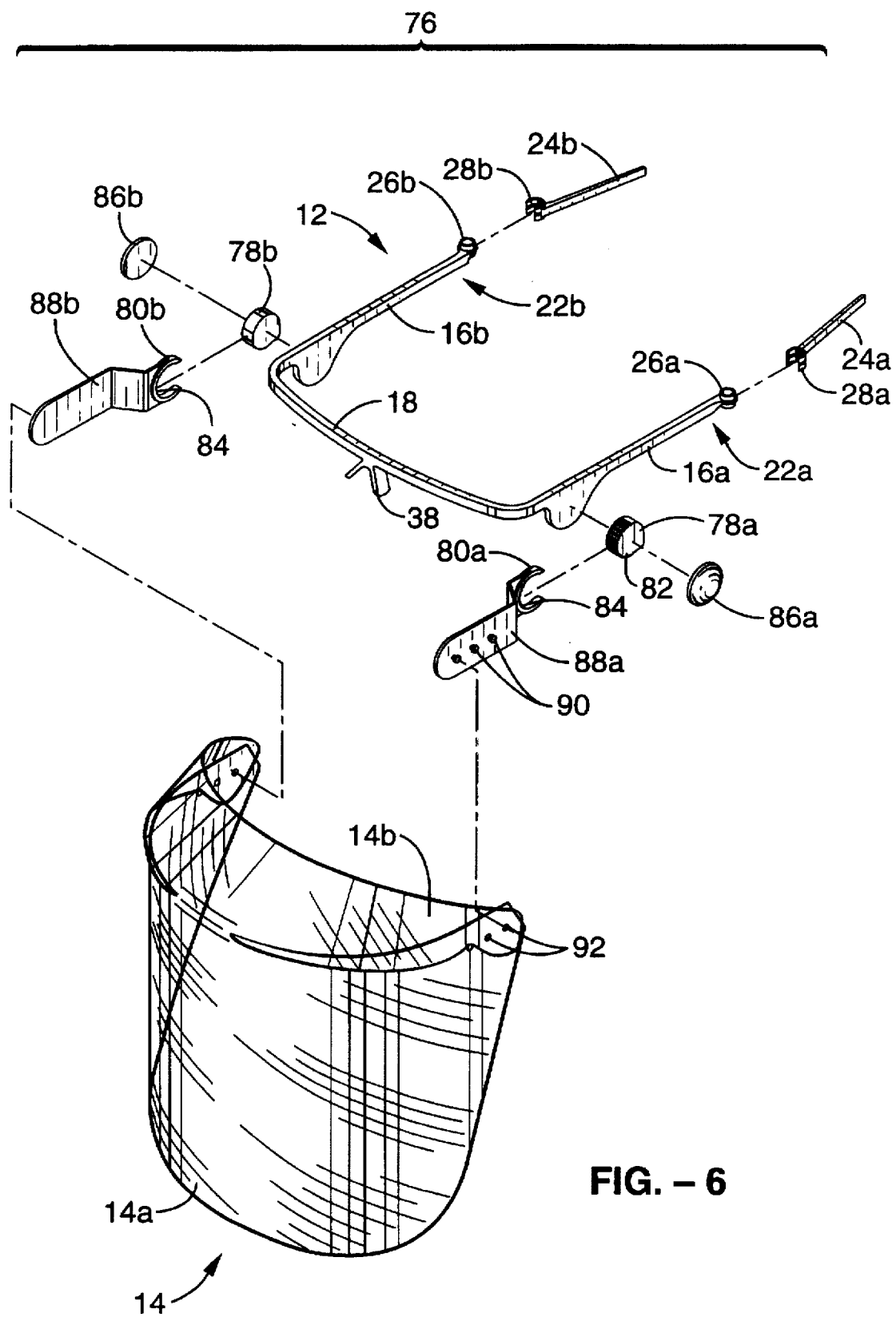
FIG. 6 is an exploded view of the face shield apparatus of FIG. 5.

Referring next to FIG. 5 and FIG. 6, there is shown a second embodiment face shield apparatus 76 in accordance with the present invention, wherein like reference numerals denote like parts. The apparatus 76 includes a frame assembly 12 and face shield 14. Face shield 14 is shown with a generally curved structure and configuration, and includes lower and upper parts 14a, 14b. Frame assembly includes first and second side members 16a, 16b coupled to a front member 18 at ends 20a, 20b. Articulating tails 24a, 24b are pivotally coupled to ends 22a, 22b of side members 16a, 16b in the manner described above.

Pivotal coupling means are included with the apparatus 76, and preferably comprise first and second posts 78a, 78b mounted on side members 16a, 16b respectively. Side members 16a, 16b are shown with a slightly different configuration than in the first embodiment 10 in order to accommodate posts 78a, 78b. First and second sockets 80a, 80b pivotally engage or receive posts 78a, 78b. A plurality of serrations or teeth 82 (FIG. 6) are included on the outer surface of post 78a, and a corresponding plurality of serrations or teeth 84 are included along the inner surface of socket 80a, with teeth 82 structured and configured to intermesh with teeth 84. Note that serrations or teeth are omitted from post 78b and socket 80b, for the reasons discussed below. Caps 86a, 86b on posts prevent sockets 80a, 80b from disengaging from posts 78a, 78b by sliding or moving laterally.

Sockets 80a, 80b are coupled to mounting pads 88a, 88b, which serve as snap fitting means for detachably coupling sockets 80a, 80b to face shield 14. A plurality of studs 90 are provided on mounting pads 88a, 88b, with studs 90 structured and configured to reversibly snap fit into a corresponding plurality of holes 92 included in top and bottom portions 14a, 14b of face shield 14.

In operation, the face shield apparatus 76 is employed in a manner similar to that outlined above for face shield apparatus 10. Studs 90 are snap fitted into holes 92 of face shield 14 which, when coupled to mounting pads 88a, 88b, assumes the curved configuration shown. Post 78a is engaged in socket 80a, and post 78b is engaged in socket 80b. Frame assembly 12 is placed on the wearer's head as described above, and articulating tails 24a, 24b are positioned to retain frame assembly 12 on the wearer's head. By pushing on face shield 14, force is exerted on the attached sockets 80a, 80b, causing sockets 80a, 80b to pivot about posts 78a, 78b respectively. As socket 80a pivots about post 78a, serrations 82, 84, which are intermeshed while resting, disengage and move relative to each other. Upon removal of force, serrations 82, 84 engage and intermesh in the adjusted position and retain the adjusted position. As discussed above, face shield 14 preferably comprises thin, resilient material which easily bends upon application of force by pushing on face shield. Thus, in order to reduce or minimize the amount of force required for positional adjustment of face shield 14 relative to frame assembly 12, serrations 82, 84 are preferably included only on first post 78a and first socket 80a, and not on second post and socket 78b, 80b. Post 78b thus pivots within socket 80b with a smooth articulating motion, while post 78a pivots within socket 80a with a ratcheting or incremental clicking motion.

The apparatus 76 is quickly and easily disassembled by generally reversing the above procedure, so that a dirty or contaminated face shield 14 may be replaced with a fresh face shield. Sockets 80a, 80b and mounting pads 88a, 88b respectively are preferably integral portions of single pieces which are made of durable, autoclavable polymeric material. When contaminated, face shield 14 may be disposed or sterilized for re-use as described above.

Figure 7:
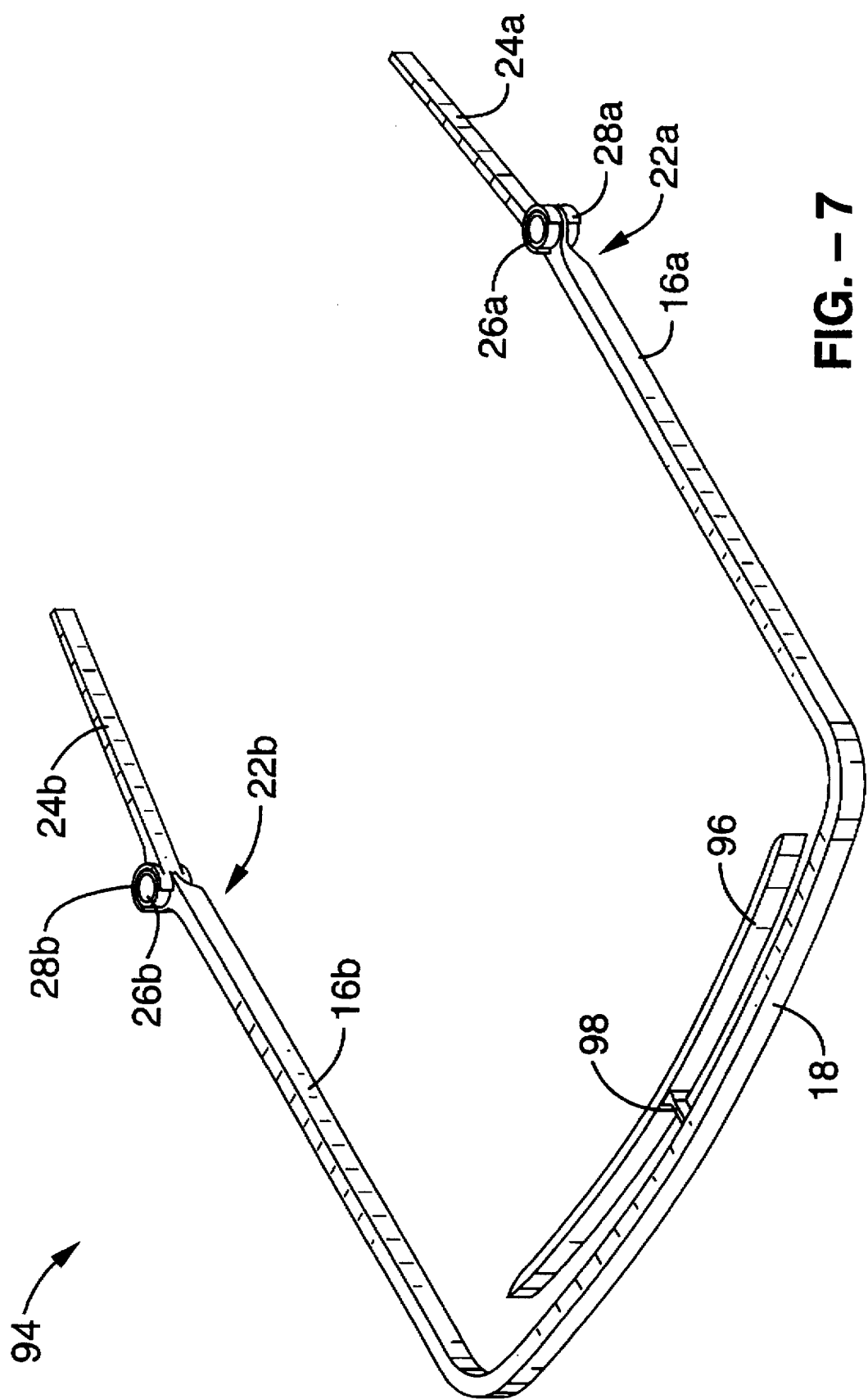
FIG. 7 is a perspective view of an alternative embodiment of a frame assembly in accordance with the invention.

Referring now to FIG. 7, an alternative embodiment 94 of a frame assembly in accordance with the invention is generally shown, wherein like reference numerals denote like parts. The frame assembly 94 is generally identical to the frame assembly 12 of apparatus 10 as described above except for the employment of a forehead support 96 as means for supporting frame assembly 12 on the wearer's face. Forehead support 96 is coupled to from member 18 by connecting portion 98, and may be used alternatively or in addition to the nose support 38 described above. Forehead support 94 preferably has an arcuate shape as shown, and is generally structured and configured to rest on the wearer's forehead just above the wearer's eye brows. Frame assembly 94 is otherwise used in the same manner as related above for frame assembly 12.

Figure 8:
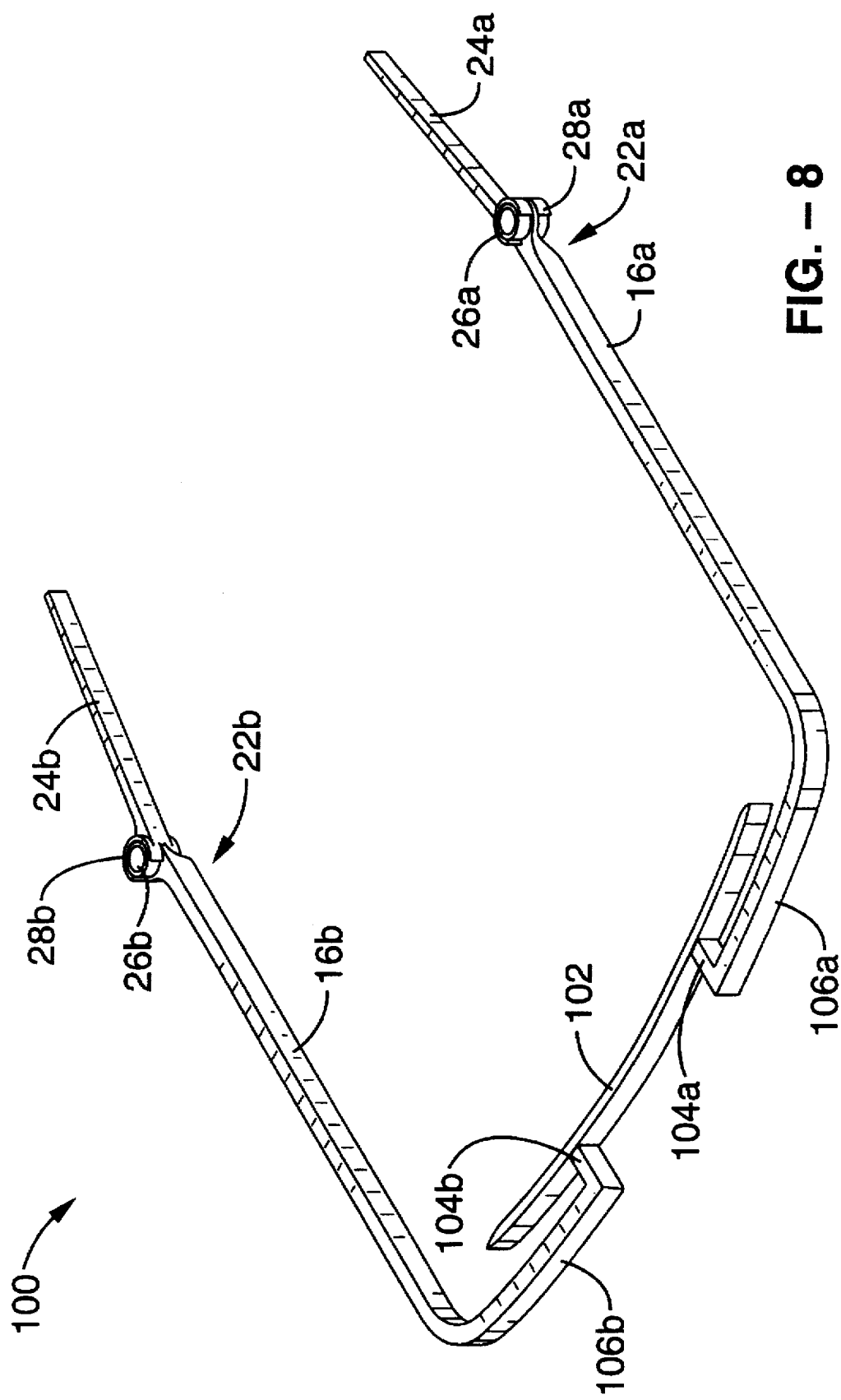
FIG. 8 is a perspective view of another alternative embodiment of a frame assembly in accordance with the invention.

Referring now to FIG. 8, there is shown yet another embodiment of a frame assembly 100 in accordance with the present invention, wherein like reference numerals denote like parts. A forehead support 102 is mounted by connecting arms 104a, 104b to front members 106a, 106b of frame assembly 100. Front members 106a, 106b are joined to side members 16a, 16b respectively. Frame assembly 100 illustrates that yet another possible structure and configuration for a frame assembly in accordance with the invention, and is used in generally the same manner as related above for frame assemblies 12 and 94.

Accordingly, it will be seen that this invention provides a face shield apparatus which is comfortable to wear, which provides for pivotal adjustment of the face shield while on the wearer's head, and which provides for quick and easy detachment and replacement of face shields. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A face shield apparatus, comprising:
   (a) a frame assembly, said frame assembly including a front member, said frame assembly including first and second side members, said first and second side members coupled to said front member;
   (b) a thin, resilient, transparent face shield;
   (c) a first cylindrical post, said first post coupled to said frame assembly;
   (d) a first socket, said first socket structured and configured to pivotally engage said post;
   (e) snap fitting means for detachably coupling said first socket to said face shield; and
   (f) first and second articulating tails, said first and second articulating tails pivotally coupled respectively to said side first and second side members.

2. A face shield apparatus as recited in claim 1, further comprising a link member, said link member including a socket, said link member including a post, said link member socket structured and configured to pivotally engage said first post on said frame assembly, said link member post structured and configured to pivotally engage said first socket.

3. A face shield apparatus as recited in claim 1, further comprising:
   (a) a second cylindrical post, said second cylindrical post coupled to said frame assembly;
   (b) a second socket, said second socket structured and configured to pivotally engage said second post; and
   (c) snap fitting means for detachably coupling said second socket to said face shield.

4. A face shield plurality as recited in claim 3, wherein said snap fitting means comprises.

5. A face shield apparatus as recited in claim 1, wherein said frame assembly further comprises a forehead support, said forehead support coupled to said front member of said frame assembly.

6. A face shield apparatus as recited in claim 1, wherein said snap fitting means comprises a mounting rod, said first socket joined to said mounting rod, said mounting rod including a plurality of studs, said face shield including a plurality of openings, said openings in said face shield reversibly snap fitting said studs on said mounting rod.

7. A face shield apparatus as recited in claim 1, further comprising a lateral ridge on said first post and a lateral groove on said first socket, said lateral ridge structured and configured to slidably engage said lateral groove.

8. A face shield apparatus as recited in claim 1, further comprising a plurality of teeth on an outer surface of said first post and a plurality of teeth on an inner surface of said first socket, said plurality of teeth on said post structured and configured to reversibly intermesh with said plurality of teeth on said first socket.

9. A face shield, comprising:
   (a) a frame assembly, said frame assembly including a front member, said frame assembly including first and second side members, said first and second side members coupled to said front member;
   (b) a thin, resilient, transparent face shield;
   (c) a first cylindrical post, said first post coupled to said frame assembly;
   (d) a first socket, said first socket structured and configured to pivotally engage said first post;
   (e) snap fitting means for attaching said first socket to said face shield; and
   (f) a forehead support, said forehead support coupled to said front member of said frame assembly.

10. A face shield apparatus as recited in claim 9, further comprising a link member, said link member including a socket, said link member including a post, said link member socket structure and configured to pivotally engage said first post on said frame assembly, said link member post structured and configured to pivotally engage said first socket.

11. A face shield apparatus as recited in claim 9, further comprising:
   (a) a second cylindrical post, said second cylindrical post coupled to said frame assembly;
   (b) a second socket, said second socket structured and configured to pivotally engage said second post; and
   (c) snap fitting means for attaching said second socket to said face shield.

12. A face shield apparatus as recited in claim 11, wherein said snap fitting means comprises first and second mounting pads, said first and second mounting pads joined respectively to said first and second sockets, said first and second mounting pads each having a plurality of studs, said face shield having plurality of holes, said holes in said face shield structured and configured to receive said studs on said mounting pads.

13. A face shield apparatus as recited in claim 9, wherein said snap fitting means comprises a mounting rod, said first socket joined to said mounting rod, said mounting rod including a plurality of studs, said face shield including a plurality of openings, said openings in said face shield reversibly snap fitting said studs on said mounting rod.

14. A face shield apparatus as recited in claim 9, further comprising a lateral ridge on said first post and a lateral groove on said first socket, said lateral ridge structured and configures to slidably engage said lateral groove.

15. A face shield apparatus as recited in claim 9, further comprising first and second articulating tails, said first and second articulating tails pivotally coupled respectively to said side first and second members.

16. A face shield apparatus, comprising:
   (a) a frame assembly, said frame assembly including a front member, said frame assembly including a pair of side members coupled to said front member;
   (b) a face shield;
   (c) a cylindrical post, said cylindrical post coupled to said frame assembly;
   (d) a socket, said socket coupled to said face shield, said socket structured and configured to pivotally engage said post; and
   (e) a link member, said link member including a socket, said link member including a post, said link member socket structured and configured to pivotally engage said post on said frame assembly, said link member post structured and configured to pivotally engage said socket on said face shield.

17. A face shield apparatus as recited in claim 16, further comprising a pair of articulating tails, one said articulating tail pivotally coupled to each said side member.

18. A face shield apparatus as recited in claim 16, wherein said frame assembly further comprises a forehead support, said forehead support coupled to said front member of said frame assembly.

19. A face shield apparatus as recited in claim 16, wherein:
   (a) said socket on said face shield includes a lateral groove;
   (b) said link socket includes a lateral groove;
   (c) said post on said frame assembly includes a lateral ridge, said lateral ridge on said post slidably engaging said lateral groove in said link socket; and
   (d) said link post includes a lateral ridge, said lateral ridge on said link post slidably engaging said lateral groove in said socket on said face shield.

20. A face shield apparatus as recited in claim 6, further comprising a mounting rod, said socket joined to said mounting rod, said mounting rod including a plurality of studs, said face shield including a plurality of openings, said openings in said face shield reversibly snap fitting said studs on said mounting rod.

21. A face shield apparatus, comprising:
   (a) a frame assembly including a front member, said frame assembly including first and second side members, said first and second side members coupled to said front member;
   (b) a thin, resilient, transparent face shield;
   (c) a first cylindrical post, said first post coupled to said frame assembly;
   (d) a first socket, said first socket structured and configured to pivotally engage said post;
   (e) snap fitting means for attaching said first socket to said face shield;
   (f) a forehead support, said forehead support coupled to said front member of said frame assembly; and
   (g) first and second articulating tails, said frame and second articulating tails pivotally coupled respectively to said first and second side members.

\* \* \* \* \*